US012807558B2

(12) United States Patent
Jeong et al.

(10) Patent No.: US 12,807,558 B2
(45) Date of Patent: Nov. 24, 2026

(54) METHOD OF MANUFACTURING DIESTER-BASED COMPOUND

(71) Applicant: LG CHEM, LTD., Seoul (KR)

(72) Inventors: Jae Hun Jeong, Daejeon (KR); Yeon Uk Choo, Daejeon (KR); Sung Kyu Lee, Daejeon (KR)

(73) Assignee: LG CHEM, LTD., Seoul (KR)

( * ) Notice: Subject to any disclaimer, the term of this patent is extended or adjusted under 35 U.S.C. 154(b) by 1038 days.

(21) Appl. No.: 17/639,447

(22) PCT Filed: Aug. 20, 2021

(86) PCT No.: PCT/KR2021/011087

§ 371 (c)(1),
(2) Date: Mar. 1, 2022

(87) PCT Pub. No.: WO2022/108051

PCT Pub. Date: May 27, 2022

(65) Prior Publication Data

US 2023/0348355 A1 Nov. 2, 2023

(30) Foreign Application Priority Data

Nov. 17, 2020 (KR) .................. KR10-2020-0154015

(51) Int. Cl.

| | |
|---|---|
| ***C07C 67/08*** | (2006.01) |
| ***B01D 17/02*** | (2006.01) |
| ***B01J 19/24*** | (2006.01) |
| ***C07C 67/48*** | (2006.01) |
| ***C07C 67/58*** | (2006.01) |

(52) U.S. Cl.

CPC .......... *C07C 67/08* (2013.01); *B01D 17/0214* (2013.01); *B01J 19/245* (2013.01); *C07C 67/48* (2013.01); *C07C 67/58* (2013.01)

(58) Field of Classification Search

CPC . B01D 17/0214; B01J 19/1862; B01J 19/245; C07C 67/08; C07C 67/48; C07C 67/58; C07C 69/82

See application file for complete search history.

(56) References Cited

U.S. PATENT DOCUMENTS

| | | | | |
|---|---|---|---|---|
| 10,239,818 | B2 | 3/2019 | Schraut et al. | |
| 2007/0161815 | A1* | 7/2007 | Osborne | C07C 67/08 560/76 |
| 2015/0141691 | A1* | 5/2015 | Disteldorf | C07C 67/08 560/99 |
| 2017/0297997 | A1 | 10/2017 | Schraut et al. | |
| 2020/0317861 | A1* | 10/2020 | Kim | B01J 19/0013 |

FOREIGN PATENT DOCUMENTS

| | | | |
|---|---|---|---|
| CN | 201670810 | * | 12/2010 |
| CN | 102256923 | A | 11/2011 |
| CN | 107935846 | A | 4/2018 |
| JP | 2001-261617 | A | 9/2001 |
| JP | 2010-516809 | A | 5/2010 |
| KR | 10-2009-0115125 | A | 11/2009 |
| KR | 10-2011-0101205 | A | 9/2011 |
| KR | 10-2013-0042742 | A | 4/2013 |
| KR | 10-1663586 | B1 | 10/2016 |
| KR | 10-2017-0078699 | A | 7/2017 |
| KR | 10-2019-0027623 | A | 3/2019 |
| KR | 10-2020-0064619 | * | 6/2020 |
| KR | 10-2020-0064619 | A | 6/2020 |
| KR | 10-2162204 | B1 | 10/2020 |
| KR | 102162204 | * | 10/2020 |
| NL | 2021197 | * | 1/2019 |
| NL | 2021197 | B1 | 1/2019 |
| WO | 2020/204558 | A1 | 10/2020 |

OTHER PUBLICATIONS

KR102162204 translation (Year: 2020).*
KR10-2020-0064619 translation (Year: 2020).*
CN201670810 translation (Year: 2010).*
International Search Report and Written Opinion issued in corresponding International Patent Application No. PCT/KR2021/011087, dated Nov. 30, 2021.
Office Action issued in Chinese Patent Application No. 202180005309.8 dated Nov. 28, 2023.
Extended European Search Report issued in corresponding European Patent Application No. 21859330.9 dated Nov. 23, 2022.

* cited by examiner

*Primary Examiner* — Andrew D Kosar
*Assistant Examiner* — Blaine G Doletski
(74) *Attorney, Agent, or Firm* — Morgan, Lewis & Bockius LLP

(57) ABSTRACT

A diester-based compound is continuously prepared in a total of n reaction units serially connected, each reaction unit includes a reactor and layer separator. The preparation includes: supplying and esterifying a feed stream including a dicarboxylic acid and an alcohol into a first reactor to prepare a reaction product, and supplying a lower draw-off stream including the reaction product into reactors of rear reaction units; supplying an upper draw-off stream of the first reactor into a first layer separator, refluxing a lower draw-off stream including an alcohol from the first layer separator into the first reactor; and supplying an upper draw-off stream of at least one reactor of second to and nth reactors into each of the layer separators, splitting a portion of the lower draw-off stream including the alcohol from each of the layer separators, and refluxing only a portion of the split stream into each of the reactors.

13 Claims, 5 Drawing Sheets

【Figure 1】
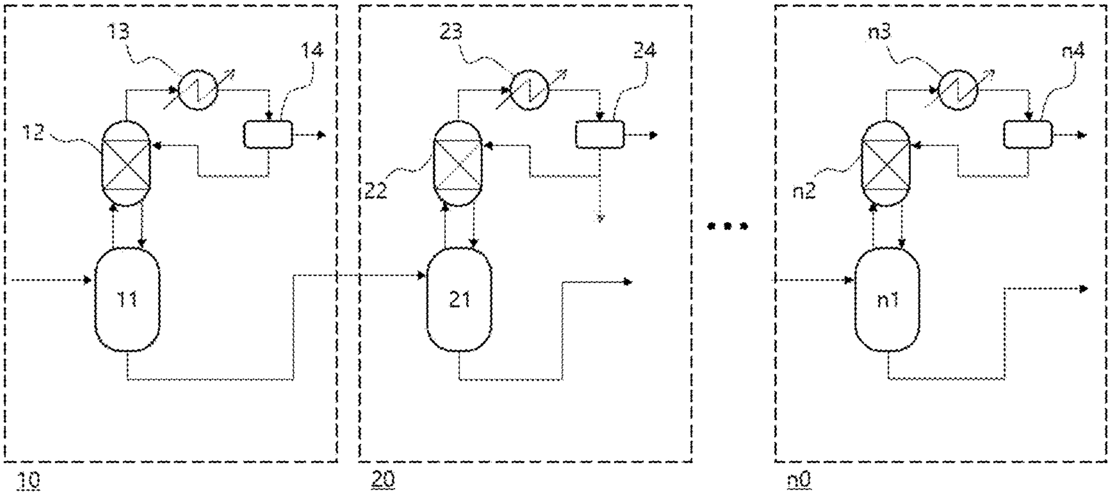
【Figure 2】
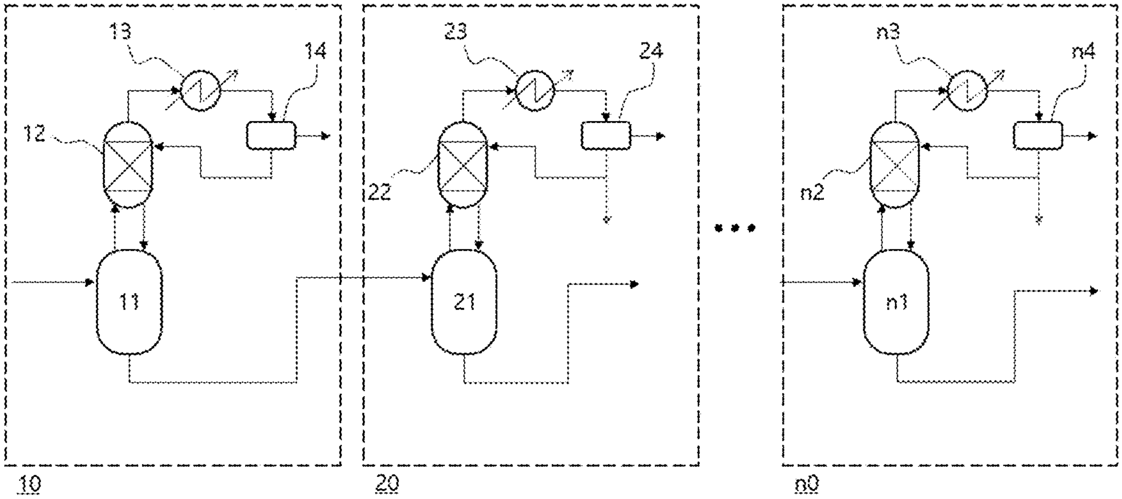

【Figure 3】
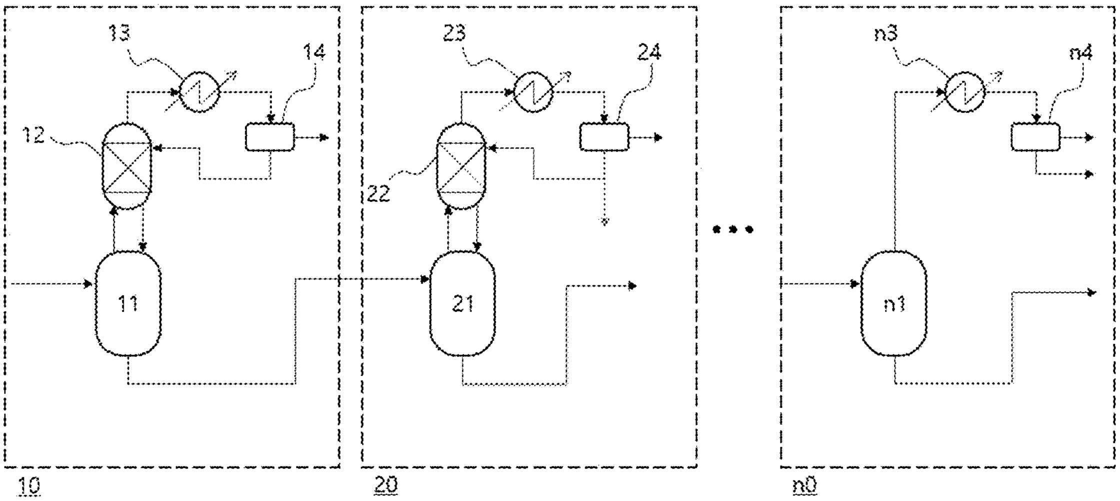
【Figure 4】
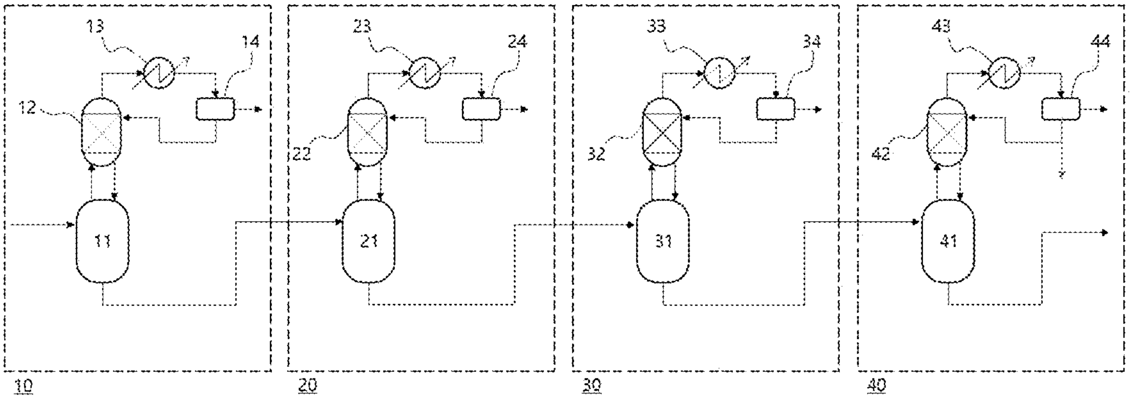

【Figure 5】
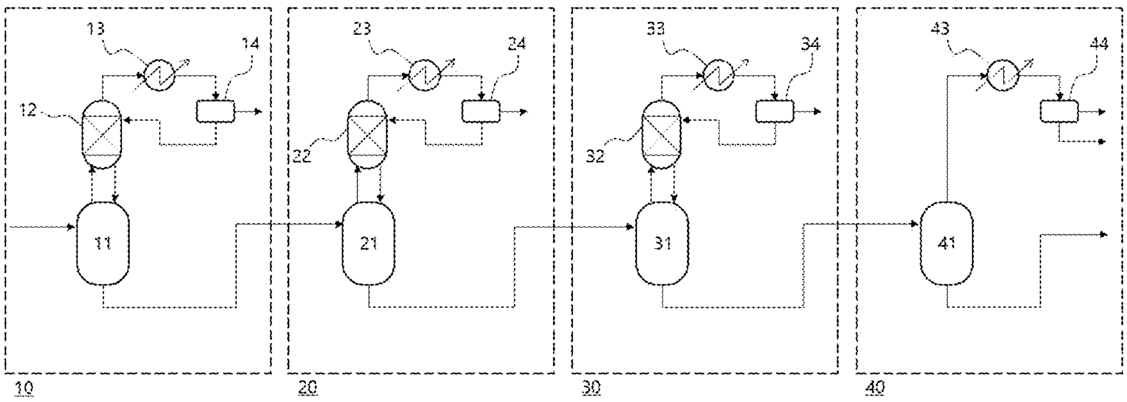
【Figure 6】
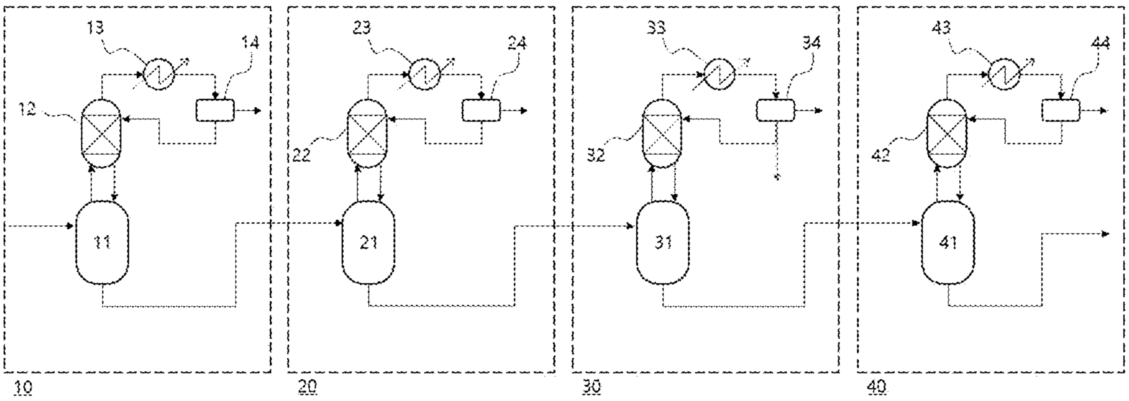

【Figure 7】
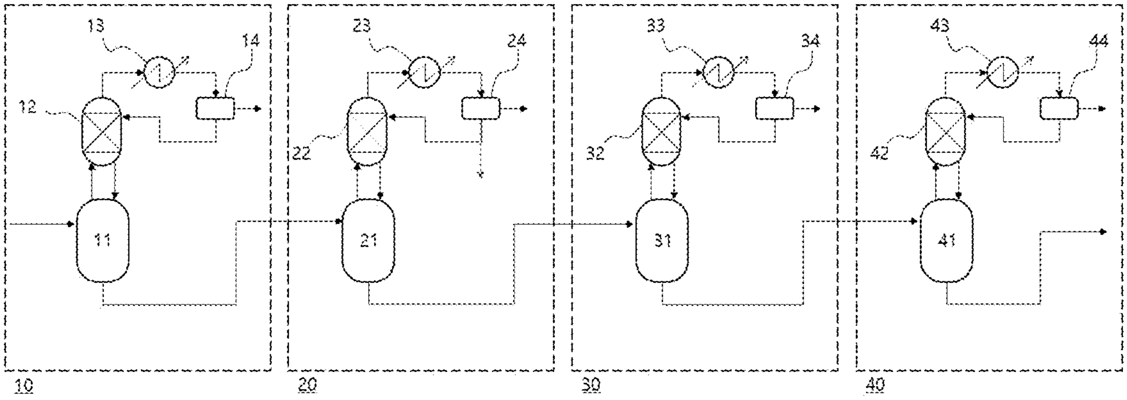
【Figure 8】
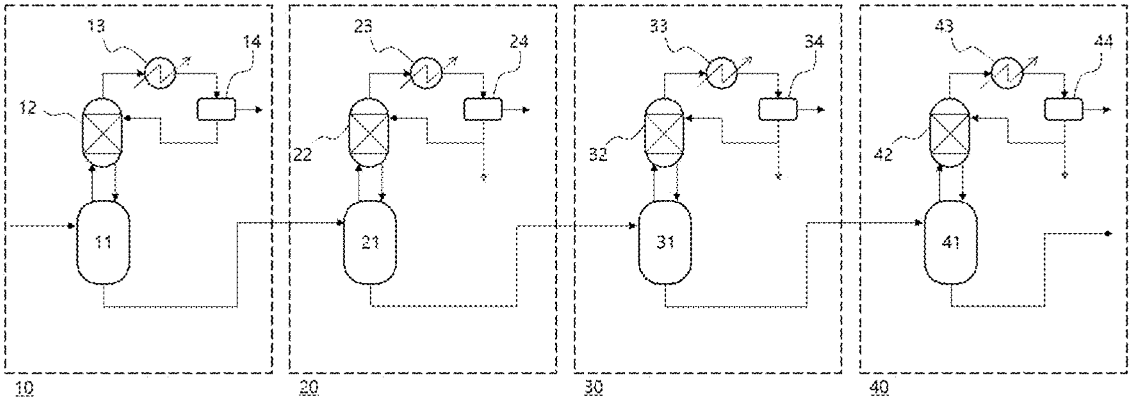

【Figure 9】
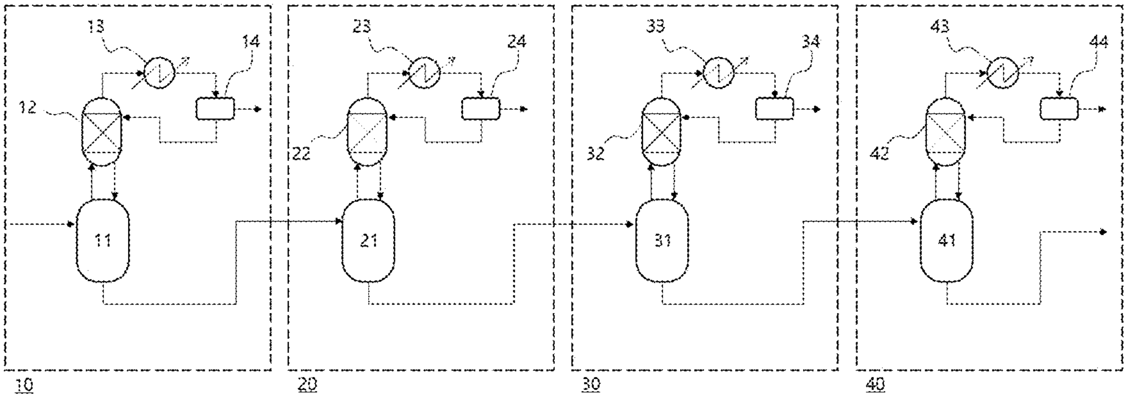

METHOD OF MANUFACTURING DIESTER-BASED COMPOUND

CROSS-REFERENCE TO RELATED APPLICATION

This application claims priority to and the benefit of Korean Patent Application No. 10-2020-0154015, filed on Nov. 17, 2020, the disclosure of which is incorporated herein by reference in its entirety.

TECHNICAL FIELD

The present invention relates to a method of manufacturing a diester-based compound, and, more particularly, to a method of manufacturing a diester-based compound capable of minimizing a size of a device and a use amount of energy supplied into a reactor when the diester-based compound is manufactured using a continuous process.

BACKGROUND ART

Phthalate-based plasticizers account for 92% of the global plasticizer market by the 20th century, and are additives that are mainly used to impart flexibility, durability, cold hardiness, and the like to polyvinyl chloride (PVC) and reduce melt viscosity to improve processability. Therefore, the phthalate-based plasticizers may be introduced into the PVC at various contents and thus widely used for applications spanning from hard products such as hard pipes to soft and stretchable materials such as food packaging materials, blood bags, flooring materials, and the like, which are closely related to the real lives and unavoidably come into direct contact to the human body among other materials.

Despite the compatibility with PVC and the excellent softness-imparting property of the phthalate-based plasticizer, however, the phthalate-based plasticizer is leaked little by little out of PVC products containing the phthalate-based plasticizer when the PVC products are used in real life. Therefore, there have been issues regarding the harmfulness of the phthalate-based plasticizer from the fact that the phthalate-based plasticizer may serve as a suspected endocrine disruptor (an environmental hormone) and a carcinogen at a level of heavy metals. In particular, since it has been reported in the USA by the 1960s that di-(2-ethylhexyl) phthalate (DEHP) which was used at the largest amount was leaked out of the PVC products, various types of research on the harmfulness of the phthalate-based plasticizer to the human body have been conducted with an increasing interest in environmental hormones in the 1990s.

Accordingly, many groups of researchers have conducted research to develop an environmentally-friendly plasticizer capable of being replaced by the di-(2-ethylhexyl)phthalate and improve a process for the environmentally-friendly plasticizer in order to deal with the environmental regulations and the environmental hormone problems caused by the leakage of diester-based phthalate-based plasticizers (particularly, di-(2-ethylhexyl)phthalate).

Meanwhile, a batch-type process has been applied as a process of manufacturing the diester-based plasticizer in most industry fields, and a system for refluxing unreacted materials in a reactor and effectively removing side-reaction products using the batch-type process has been developed. However, the manufacturing of the diester-based plasticizer using the batch-type process has limitations on an improvement of a reflux rate or an amount of steam, has very low productivity, and also has technical limitations applicable to solve the problems.

DISCLOSURE

Technical Problem

To solve the problems as mentioned above in the background art of the present invention, an object of the present invention is to provide a method of manufacturing a diester-based compound capable of minimizing a size of a device and a use amount of energy supplied into a reactor, wherein the diester-based compound is manufactured as an environmentally-friendly plasticizer using a continuous process.

Technical Solution

In one general aspect, a method of manufacturing a diester-based compound is performed using a continuous process including a reaction part in which a total of n reaction units spanning from a first reaction unit to an $n^{th}$ reaction unit are connected in series, wherein each of the reaction units includes a reactor and a layer separator, and the method includes: supplying a feed stream including a dicarboxylic acid and an alcohol into the first reactor, esterifying the feed stream to prepare a reaction product, and supplying a lower discharge stream including the reaction product into the reactors of the rear reaction units (S10); supplying an upper discharge stream of the first reactor into a first layer separator, and refluxing a lower discharge stream including an alcohol from the first layer separator into the first reactor (S20); and supplying an upper discharge stream of at least one reactor of second to and $n^{th}$ reactors into each of the layer separators, splitting a portion of the lower discharge stream including the alcohol from each of the layer separators, and refluxing only a portion of the split stream into each of the reactors (Step (S30)).

Advantageous Effects

According to the present invention, when a diester-based compound is manufactured using a continuous process, an excess ratio of an alcohol in each of reactors can be kept constant by supplying an upper discharge stream of at least one reactor of second to $n^{th}$ reactors into each of layer separators, splitting a portion of a lower discharge stream including an alcohol from each of the layer separators, and refluxing only a portion of the split stream into each of the reactors, thereby minimizing a size of a device and a use amount of energy supplied into the reactors.

DESCRIPTION OF DRAWINGS

FIGS. 1 to 8 are process flow charts of methods of manufacturing a diester-based compound according to one embodiment of the present invention, respectively.

FIG. 9 is a process flow chart of a method of manufacturing a diester-based compound according to Comparative Example 1 of the present invention.

BEST MODE

Prior to the description, it should be understood that the terms and words used in the specification and the appended claims should not be construed as limited to general and dictionary meanings, but interpreted based on the meanings and concepts corresponding to technical aspects of the present invention on the basis of the principle that the present inventors can appropriately define the concepts of terms for the purpose of describing the present invention in the best way.

In the present invention, the term "upper" may refer to a region that corresponds to a height of 50% or more from the entire height of a device in a vessel, and the term "lower" may refer to a region that corresponds to a height of less than 50% of the entire weight of the device and the vessel.

In the present invention, the term "stream" may refer to a flow of a fluid during a process, and may also refer to a fluid itself that flows in pipes. Specifically, the "stream" may refer to both a fluid itself and a flow of the fluid that flows in a pipe connecting respective devices. Also, the fluid may refer to a gas or a liquid. It is not intended to exclude any case in which solid contents are included in the fluid.

Hereinafter, the present invention will be described in further detail with reference to FIGS. 1 to 9 in order to aid in understanding the present invention.

According to the present invention, a method of manufacturing a diester-based compound is provided. Referring to FIGS. 1 and 2 below, the method of manufacturing a diester-based compound is performed using a continuous process including a reaction part in which a total of n reaction units 10, 20, and n0 spanning from a first reaction unit 10 to an $n^{th}$ reaction unit n0 are connected in series, wherein each of the reaction units 10, 20, and n0 includes each of reactors 11, 21, and n1 spanning from a first reactor 11 to an $n^{th}$ reactor n1, and each of layer separators 14, 24, and n4 spanning from a first layer separator 14 to an $n^{th}$ layer separator n4, and the method includes: supplying a feed stream including a dicarboxylic acid and an alcohol into the first reactor 11, esterifying the feed stream to prepare a reaction product, and supplying a lower discharge stream including the reaction product into the reactors of the rear reaction units (S10); supplying an upper discharge stream of the first reactor 11 into a first layer separator, and refluxing a lower discharge stream including an alcohol from the first layer separator into the first reactor 11 (S20); and supplying an upper discharge stream of at least one reactor of a second reactor 21 to an $n^{th}$ reactor n1 into each of the layer separators, splitting a portion of the lower discharge stream including the alcohol from each of the layer separators, and refluxing only a portion of the split stream into each of the reactors (Step (S30)).

According to one embodiment of the present invention, the manufacturing of the diester-based compound may be performed using a continuous process including a reaction part in which a total of n reaction units 10, 20 and n0 spanning from a first reaction unit 10 to an $n^{th}$ reaction unit n0 are connected in series.

Specifically, a batch-type manufacturing process was applied to the manufacturing of the diester-based compound as known in the prior art. However, the manufacturing of the diester-based compound using the batch-type process has limitations on an amount of the reflux or the steam, has very low productivity, and also has technical limitations applicable to solve the problems.

Also, in order to solve the above-described problems of the batch-type process, a continuous manufacturing process in which two or more reactors are connected in series during the manufacturing of the diester-based compound to constitute a reaction part has been developed. In this case, in order to maintain an excess ratio of the alcohol to the dicarboxylic acid in the reactor to secure the reactivity, all of a stream including an alcohol vaporized from an upper portion of each of reactors was refluxed into each of the reactors. In this case, an amount of the dicarboxylic acid decreases toward the rear reactors, but an excess ratio of the alcohol increases. Therefore, the continuous manufacturing process has drawbacks in that a use amount of energy required to vaporize an excessive amount of the alcohol in each of the reactors increases, and a size of a device required to process such an excessive evaporation amount of the alcohol inevitably increases, resulting in an increased installation cost.

Therefore, when the diester-based compound is manufactured using the continuous process according to the present invention, an excess ratio of an alcohol in each of reactors may be maintained constant by supplying an upper discharge stream of at least one reactor of second to $n^{th}$ reactors into each of layer separators, splitting a portion of a lower discharge stream including an alcohol from each of the layer separators, and refluxing only a portion of the split stream into each of the reactors, thereby minimizing a size of a device and a use amount of energy supplied into the reactors.

In the present invention, the term "excess ratio" may refer to a ratio of an alcohol which is present in an excessive amount based on the mole ratio of the dicarboxylic acid and the alcohol stoichiometrically required in the reactor in order to secure the reactivity.

According to one embodiment of the present invention, each of the reaction units may include a total of n reactors spanning from a first reactor to an $n^{th}$ reactor. As a specific example, each of the reactors may be a reactor used to esterify a dicarboxylic acid and an alcohol.

The esterification reaction may be a reaction in which a dicarboxylic acid and an alcohol are supplied into a reactor and are directly esterified in the presence of a catalyst. As such, a diester-based compound and water as a by-product may be generated through the esterification reaction of the dicarboxylic acid and the alcohol. The operating temperature, the operating pressure, the time, and the type and content of the catalyst, which may be used to perform the direct esterification reaction, may be directly applied as the conventional conditions applied as in the prior art, or may be applied after they are properly adjusted according to the process operations, when necessary.

The dicarboxylic acid and the alcohol may be mixed using a pre-mixer and introduced as a mixture in batches before the dicarboxylic acid and the alcohol are supplied into the reactor, or may be introduced in batches into the reactors provided with separate feed lines, respectively.

The dicarboxylic acid may, for example, include one or more selected from the group consisting of aromatic polyhydric carboxylic acids such as phthalic acid, isophthalic acid, terephthalic acid, trimellitic acid, and the like; and saturated or unsaturated, aliphatic polyhydric carboxylic acids such as adipic acid, sebacic acid, azelaic acid, succinic acid, maleic acid, fumaric acid, and the like. As a specific example, the dicarboxylic acid may be terephthalic acid.

For example, the alcohol may be a monohydric alcohol having 4 to 13, 5 to 12, or 6 to 10 carbon atoms. For example, the monohydric alcohol may include straight or branched chain alcohols such as n-butyl alcohol, isobutyl alcohol, secondary butyl alcohol, n-pentyl alcohol, n-hexyl alcohol, n-heptyl alcohol, n-octyl alcohol, 2-ethylhexanol, iso-octyl alcohol, iso-nonyl alcohol, n-nonyl alcohol, isodecyl alcohol, n-decyl alcohol, undecyl alcohol, tridecyl alcohol, and the like. As a specific example, the alcohol may be 2-ethylhexanol.

An excessive amount of the alcohol may be supplied into the reactor, based on a stoichiometric amount required to react with the dicarboxylic acid. For example, in the esterification reaction, a mole ratio of the dicarboxylic acid and the alcohol may be in a range of 1:2 to 1:10, 1:2 to 1:5, or 1:2 to 1:4.5. Accordingly, the mole ratio of the dicarboxylic acid and the alcohol in the feed stream supplied into the first reactor 11 may be in a range of 1:2 to 1:10, 1:2 to 1:5, or 1:2 to 1:4.5. When the dicarboxylic acid and the alcohol are supplied as the reactants into the first reactor 11 in the mole ratio range, a desired conversion rate may be easily reached by minimizing a use amount of steam and controlling a forward reaction rate of the esterification reaction.

For example, the catalyst may include one or more selected from the group consisting of acid catalysts such as sulfuric acid, para-toluenesulfonic acid, methanesulfonic acid, and the like; alkyl titanate catalysts such as tetraisopropyl titanate, tetrabutyl titanate, tetra-2-ethylhexyl titanate, and the like; and organic metal catalysts such as dibutyl tin oxide, butyl tin malate, and the like. As a specific example, an organic titanium compound representative as the alkyl titanate may be used as the catalyst. In this way, a reaction time may be shortened by increasing an esterification reaction rate.

The operating temperature of the reactor may, for example, be in a range of 130 to 250° C., 140 to 240° C., or 150 to 230° C. In this case, the operating temperature of the reactor may individually refer to an operating temperature of the reactor in each of the first reaction unit to the $n^{th}$ reaction unit. More specifically, the reactor of each of the first reaction unit to the $n^{th}$ reaction unit may be equally or individually controlled in the temperature range.

The operating pressure of the reactor may be in a range of 0 to 4 kg/cm$^2$G, 0 to 2 kg/cm$^2$G, or 0 to 1 kg/cm$^2$G. In this case, the operating pressure of the reactor may individually refer to an operating pressure of the reactor in each of the first reaction unit to the $n^{th}$ reaction unit. More specifically, the reactor of each of the first reaction unit to the $n^{th}$ reaction unit may be equally or individually controlled in the pressure range.

According to one embodiment of the present invention, the dicarboxylic acid may be terephthalic acid, and the alcohol may be 2-ethylhexanol. As such, when terephthalic acid and 2-ethylhexanol are introduced into the reactor in the presence of a catalyst to perform an esterification reaction, dioctyl terephthalate (DOTP) may be manufactured as the diester-based material. The dioctyl terephthalate is a substance that is widely used as a non-toxic environmentally-friendly plasticizer, and thus may exhibit excellent compatibility with polymer materials such as PVC, and the like, and may have excellent characteristics such as low volatility and electrical characteristics.

According to one embodiment of the present invention, each of the reaction parts is composed of a total of n reaction units which are connected in series, and may be designed in consideration of the controlled conversion rate of the reaction, the retention time in each of the reaction units, and the like, and may also be designed in consideration of the composition of a product to be achieved. For example, n may be in a range of 2 to 8, 3 to 7, or 4 to 6. That is, each of the reaction parts may include 2 to 8, 3 to 7, or 4 to 6 reaction units.

According to one embodiment of the present invention, the reaction units 10, 20, 30, 40, and n0 may further include columns 12, 22, 32, 42, and n2 in which an upper discharge stream of the reactor including an alcohol and water vaporized during an esterification reaction is received from the reactors 11, 21, 31, 41, and n1 to perform a gas/liquid separation, through which a gas phase is supplied as an upper discharge stream into layer separators 14, 24, 34, 44, and n4 by passing through condensers 13, 23, 33, 43, and n3 and a liquid phase is supplied as a lower discharge stream into the reactors 11, 21, 31, 41, and n1; and layer separators 14, 24, 34, 44, and n4 configured to separate a water layer and an alcohol layer to reflux only the alcohol into the columns and remove water.

Also, as shown in FIG. 3, the columns may be included in the first reaction unit to the n−1$^{st}$ reaction unit, and may not be included in the $n^{th}$ reaction unit, when necessary.

In the reactor, a diester-based compound, which is a reaction product through an esterification reaction of the dicarboxylic acid and the alcohol, and water as a by-product involved in the esterification reaction may be generated. For example, the reaction product of the esterification reaction may include a diester-based compound, water, and unreacted materials.

To increase a forward reaction rate of the esterification reaction, water that is the by-product should be effectively removed to prevent an inverse reaction caused by water and a deactivation of the catalyst. In this regard, as a method of removing water as the by-product, there is a method of vaporizing and drawing off water. When the water is vaporized, the alcohol having a higher boiling point than water is also vaporized due to the high reaction temperature. In this case, the vaporized alcohol may be recovered and refluxed back into the reactor to maintain high concentrations of the reactants in the reactors and remove water.

Specifically, as an esterification reaction occurs at a temperature higher than the boiling point of the alcohol while performing the esterification reaction in the reactors, the alcohol that is vaporized without participating in the reaction may inevitably exist. At the same time, because water is generated as the by-product other than the reaction product (i.e., a diester-based compound), water may be drawn off as an upper discharge stream in the reactor while vaporizing water together with the alcohol. The vaporized water and alcohol may be drawn off as an upper discharge stream of the reactor, and may be supplied into the column.

In the column, the gas-phase alcohol and water introduced from the reactors may be liquefied by the low-temperature liquid-phase alcohol supplied from the layer separators into an upper portion of the column, and most of the gas-phase alcohol may be selectively liquefied and drawn off as a lower discharge stream in the column. In this case, the lower discharge stream of the column including the liquid-phase alcohol may be introduced back into an upper portion of the reactor, and the liquid-phase alcohol may participate in the esterification reaction again.

As such, the forward reaction rate may be enhanced by passing the upper discharge stream of the reactor through the column to prevent water included in the upper discharge stream of the reactor from condensing and being introduced back into the reactors.

Also, the alcohol that has been vaporized from the reactor may be refluxed back into the reactors to maintain an excess ratio of the alcohol with respect to the dicarboxylic acid in the reactors, and water that is the by-product of the esterification reaction may be drawn off from the reaction system and removed to prevent water from being refluxed into the reactors, thereby preventing a decrease in reaction rate in the reactors and a degradation of performance of the catalyst.

Meanwhile, the gas-phase water and the non-liquefied gas-phase alcohol in the column may be drawn off as an upper discharge stream of the column, and the upper discharge stream of the column may pass through the condenser and be supplied into the layer separators. Specifically, in the layer separators or before introduction into the layer separators, the gas-phase alcohol and water need to be liquefied. Therefore, any region of a line through which the upper discharge stream of the column is transferred to the layer separator is provided with the condenser, and the gas-phase alcohol and water may be liquefied before introduction into the layer separators by removing heat of the gas-phase alcohol and water through the condenser.

The layer separation in the layer separators may be performed using a difference in densities between the alcohol and water. As a specific example, because the alcohol has a lower density than water, an alcohol layer may be formed in an upper portion of the layer separator, and a water layer may be formed in a lower portion of the layer separator. As such, after the water layer and alcohol layer are separated in the layer separators, only the alcohol may be selectively separated from the alcohol layer through a line connected to an upper portion of the column, and refluxed into the column. Also, water may be removed through a draw-off line through which water is drawn off from the water layer, or may be recycled through various routes.

As the alcohol whose temperature is reduced by condensation in the column is refluxed into the reactors, an internal temperature of the reactors may be reduced. Therefore, the calorie may be separately supplied into the reactors by supplying energy of high-pressure steam or high-temperature steam in order to maintain the internal temperature of the reactors. Because the high-pressure steam has an equilibrium temperature (a high temperature) with a high pressure, the calorie may be supplied into the reactors by supplying the high-pressure steam.

The reaction product in the reactor may be separated from the lower discharge stream of the reactor, and the lower discharge stream of each of the reactors of the first reaction unit to the $n-1^{st}$ reaction unit may be supplied into the reactors of the rear reaction units among the respective reaction units. Also, the lower discharge stream in the reactor of the $n^{th}$ reaction unit that is the last reaction unit may be separated, refined, and manufactured into products. Specifically, the lower discharge stream of each of the first reactor, which is the reactor of the first reaction unit, to the $n-1^{st}$ reactor, which is the reactor of the $n-1^{st}$ reaction unit, may be supplied into the reactor of each of the rear reaction units among the respective reaction units, and the lower discharge stream in the $n^{th}$ reactor that is the reactor of the last reaction unit (an $n^{th}$ reaction unit) may be separated, refined, and manufactured into products.

For example, as shown in FIG. 4, when a reaction part in which 4 reaction units are connected in series is included to manufacture the diester-based compound, the lower discharge stream of the first reactor 11 that is the reactor of the first reaction unit 10 may be supplied into a second reactor 21 that is a reactor of a second reaction unit 20, the lower discharge stream of the second reactor 21 may be supplied into a third reactor 31 that is the reactor of a third reaction unit 30, the lower discharge stream of the third reactor 31 may be supplied into a fourth reactor 41 that is a reactor of a fourth reaction unit 40, and the lower discharge stream of the fourth reactor 41 that is the reactor of the fourth reaction unit 40 may be separated, refined, and manufactured into products.

According to one embodiment of the present invention, a lower portion of each of the reactors may be provided with a lower draw-off line in order to transfer the lower discharge stream of each of the reactors of the reaction units 10, 20, 30, 40, and n0 into the reactors of the rear reaction units or transfer the lower discharge stream for subsequent separation and refinement processes. In addition, the lower draw-off line may be provided with a pump (not shown).

The diester-based compound included in the lower discharge stream of the $n^{th}$ reactor that is the reactor of the last reaction unit may be refined using a method known in the art. For example, when an esterification reaction is performed using an organic titanium compound as the catalyst, water is added to the obtained diester-based compound to deactivate the catalyst, and the remaining unreacted alcohol may be removed by evaporation by distilling the lower discharge stream with water vapor. Also, the remaining dicarboxylic acid may be neutralized by treatment with an alkaline material. Also, the solids may be removed by filtration to obtain a high-purity diester-based compound.

According to one embodiment of the present invention, the method of manufacturing a diester-based compound may include: supplying a feed stream including a dicarboxylic acid and an alcohol into the first reactor 11, esterifying the feed stream to prepare a reaction product, and supplying a lower discharge stream including the reaction product into the reactors of the rear reaction units (S10); supplying an upper discharge stream of the first reactor 11 into a first layer separator, and refluxing a lower discharge stream including an alcohol from the first layer separator into the first reactor 11 (S20); and supplying an upper discharge stream of at least one reactor of second to and $n^{th}$ reactors into each of the layer separators, splitting a portion of the lower discharge stream including the alcohol from each of the layer separators, and refluxing only a portion of the split stream into each of the reactors (Step (S30)).

According to one embodiment of the present invention, the upper discharge stream including an alcohol and water may be supplied from each of the reactors into the columns 12, 22, 32, 42, and n2 to perform a gas/liquid separation, the gas phase may be supplied as the upper discharge stream into the layer separators 14, 24, 34, 44, and n4 after the gas phase is condensed by passing through the condensers 13, 23, 33, 43, and n3, and the liquid phase may be supplied as the lower discharge stream into each of the reactors.

According to one embodiment of the present invention, the upper discharge stream including an alcohol and water may be supplied from the first to $n-1^{st}$ reactors into the columns to perform a gas/liquid separation, the gas phase may be condensed and supplied as the upper discharge stream into the layer separators, and the liquid phase may be supplied as the lower discharge stream into each of the reactors.

According to one embodiment of the present invention, the water layer and the alcohol layer may be separated in the layer separators, only the lower discharge stream including the alcohol may be supplied into an upper portion of the column to pass through the column, and then refluxed into each of the reactors. Then, water may be removed, or may be recycled through various routes.

As described above, in a conventional process of continuously manufacturing a diester-based compound as known in the art, all of the stream including the alcohol vaporized from each of the reactors was refluxed into each of the reactors in order to maintain an excess ratio of the alcohol to the dicarboxylic acid in the reactor to secure the reactivity. In this case, an amount of the reactant decreases toward the rear reactors, but an excess ratio of the alcohol increases. Therefore, the process of continuously manufacturing a diester-based compound has drawbacks in that a use amount of energy required to vaporize an excessive amount of the alcohol in each of the reactors increases, and a size of a device required to process such an excessive evaporation amount of the alcohol inevitably increases, resulting in an increased installation cost.

In this regard, according to the present invention, the excess ratio of the alcohol in each of reactors may be kept constant by supplying all of the upper discharge stream of the first reactor 11 into the first layer separator, refluxing all of the lower discharge stream including an alcohol from the first layer separator into the first reactor 11, supplying the upper discharge stream of at least one reactor of the second reactor 21 to the $n^{th}$ reactor n1 into each of the layer separators, splitting a portion of the lower discharge stream including the alcohol from each of the layer separators, and refluxing only a portion of the split stream into each of the reactors, thereby minimizing a size of a device and a use amount of energy supplied into the reactors.

In Step (S30), after a portion of the lower discharge stream including the alcohol is split into each of the layer separators and only a portion of the split stream is refluxed into each of the reactors, a mole ratio of the dicarboxylic acid and the alcohol in each of the reactors may be in a range of 1:2 to 1:10, 1:2 to 1:5, or 1:2 to 1:4.5. That is, as described above, only a portion of the split stream may be refluxed from the layer separators without refluxing all of the lower discharge stream including the alcohol into each of the reactors. In this case, only a portion of the split stream may be refluxed so that the mole ratio of the dicarboxylic acid and the alcohol in each of the reactors falls within the above range.

In this case, the excess ratio of the alcohol to the dicarboxylic acid included in the feed stream may be kept constant without any increase toward the rear reactors. Therefore, a desired conversion rate in the $n^{th}$ reactor n1, which is the last reactor, may be easily reached while minimizing an amount of steam supplied into each of the reactors.

According to one embodiment of the present invention, the at least one reactor may be, for example, a reactor in which a conversion rate reaches 50 to 99% among the second reactor to the $n^{th}$ reactor, but the present invention is not limited thereto.

Also, a ratio (a draw-off ratio) of a flow rate of the lower discharge stream of the layer separator drawn off without being refluxed into each of the reactors to a flow rate of the entire lower discharge stream including the alcohol from the layer separator of each of the reactors may be adjusted according to the reaction conditions such as the temperature and pressure of the reactors, the retention time of the reactants, and the like, in addition to the conversion rate of the reactor from which a feed stream starts to be drawn off in the second to $n^{th}$ reactors. Also, a use amount of energy during the process may be minimized, compared to when the draw-off is not performed.

According to one embodiment of the present invention, for example, Step (S30) may include: splitting a portion of the lower discharge stream including an alcohol from each of the layer separators in each of the reactors, which span from the reactor in which the conversion rate reaches 50 to 99% to the $n^{th}$ reactor n1 among the second reactor 21 to the $n^{th}$ reactor n1, from each of the layer separators, and refluxing only a portion of the split stream into each of the reactors. For example, as shown in FIG. 8, after the lower discharge stream of the first layer separator 14 passes through the first column 12, all of the lower discharge stream of the first layer separator 14 may be refluxed into the first reactor 11, and a portion of the lower discharge stream including the alcohol may be split from each of the layer separators 24, 34, and 44 in each of the reactors, which span from the second reactor 21 in which the conversion rate reaches 50 to 99% to the fourth reactor 41, and only a portion of the split stream may be refluxed into each of the reactors. In this case, only a portion of the split stream from each of the layer separators 24, 34, and 44 may be refluxed into each of the reactors, and the residual stream may be drawn off to the outside.

The reactor in which the conversion rate reaches 50 to 99% among the second reactor 21 to the $n^{th}$ reactor n1 may vary according to the initiation conditions for the esterification reaction, and the like, but is not limited to the second reactor 21.

Specifically, when a point of time (i.e., a draw-off point of time) at which a portion of the lower discharge stream including the alcohol is split from each of the layer separators and only a portion of the split stream is refluxed into each of the reactors is greater than or equal to a conversion rate of 50%, there is an effect of easily reaching a desired conversion rate in the $n^{th}$ reactor that is the last reactor. Meanwhile, the point of time at which a portion of the lower discharge stream including the alcohol is split from each of layer separators and only a portion of the split stream is refluxed into each of the reactors is less than or equal to a conversion rate of 99%, an amount of steam used for the entire process may be reduced, which is effective in reducing a use amount of energy.

According to one embodiment of the present invention, in Step (S30), a portion of the lower discharge stream including the alcohol may be split from each of the layer separators and only a portion of the split stream may be refluxed into each of the reactors, and the residual stream of the lower discharge stream in each of the layer separators may be recycled as the feed stream. Also, when all of the lower discharge stream including the alcohol may be drawn off from the layer separators, all of the lower discharge stream of the layer separator may be recycled as the feed stream.

According to one embodiment of the present invention, devices such as a distillation column, a condenser, a reboiler, a valve, a pump, a separator, a mixer, and the like may be further installed in the method of manufacturing a diester-based compound, when necessary.

As described above, the method of manufacturing a diester-based compound according to the present invention has been described and shown with reference to the drawings. However, the above description and the illustration of the drawings are presented to describe and illustrate only the core configuration to understand the present invention. Thus, in addition to the processes and devices described and illustrated herein, processes and devices which are not described or illustrated in any separate manners may be properly applied and used to put practice into the method of manufacturing a diester-based compound according to the present invention.

Hereinafter, the present invention will be described in further detail with reference to embodiments thereof. However, it will be apparent to those skilled in the art that the following embodiments are given for the purpose of illustrating the present invention, and may be variously modified and changed without departing from the technical spirit and scope of the present invention, but are not indeed to limit the scope of the present invention.

EXAMPLES

Examples 1-1 to 1-4

A process of manufacturing dioctyl terephthalate (DOTP) was simulated using a commercially available process simulation program ASPEN PLUS (AspenTech) according to the process flow chart as shown in FIG. 4.

Specifically, a feed stream including terephthalic acid (TPA) and 2-ethylhexanol (2-EH) at a mole ratio of 1:2 to 4.5 was supplied into a first reactor 11 that was a reactor of a first reaction unit 10, and esterified in the presence of a catalyst to reflux all of a lower discharge stream including an alcohol from a layer separator 14 into the reactor 11 and remove water from an upper discharge stream vaporized in the first reactor 11 using a column 12, a condenser 13, and the layer separator 14. Also, the lower discharge stream including the reaction product was supplied from the first reactor 11 into a second reactor 21 that was a reactor of a second reaction unit 20.

As in the operation flow in the first reaction unit 10, a continuous stirred tank reactor (CSTR) was operated through a second reaction unit 20, a third reaction unit 30, and a fourth reaction unit 40, and a lower discharge stream of a fourth reactor 41 that was a reactor of the last fourth reaction unit 40 was separated and refined to obtain dioctyl terephthalate.

In this case, a portion of the lower discharge stream including the alcohol was split from a layer separator in the fourth reactor 41 of the fourth reaction unit 40, and only a portion of the split stream was supplied into an upper portion of a fourth column 42 and passed through the fourth column 42. Thereafter, the portion of the split stream was refluxed into the fourth reactor 41, and a residual portion of the lower discharge stream of the layer separator, which was drawn off to the outside without being refluxed into the fourth reactor 41, was recycled as the feed stream of the first reactor 11.

In particular, as shown in FIG. 5, the upper discharge stream vaporized in the fourth reactor 41 was not supplied into a column in the fourth reaction unit 40 in the case of Example 1-4, and all of the lower discharge stream including the alcohol was drawn off from a layer separator 44 using a condenser 43 and a layer separator 44. Then, the feed stream of the first reactor 11 was recycled, and water was removed.

Table 1 below lists the final conversion rate according to the draw-off ratio, which is a ratio of the flow rate of the lower discharge stream of the layer separator, which is drawn off to the outside without being refluxed into the fourth reactor 41, to the flow rate of the entire lower discharge stream including an alcohol from the layer separator of the fourth reactor 41, and a use amount of steam used during the entire process. In this case, the use amount of steam is represented by a relative amount with respect to a use amount (100.0%) of steam measured in Comparative Example 1 below.

Examples 2-1 to 2-6

A process of manufacturing dioctyl terephthalate (DOTP) was simulated using a commercially available process simulation program ASPEN PLUS (AspenTech) according to the process flow chart as shown in FIG. 6.

Specifically, a feed stream including terephthalic acid (TPA) and 2-ethylhexanol (2-EH) at a mole ratio of 1:2 to 4.5 was supplied into a first reactor 11 that was a reactor of a first reaction unit 10, and esterified in the presence of a catalyst to reflux all of a lower discharge stream including an alcohol from a layer separator 14 into the reactor 11 and remove water from an upper discharge stream vaporized in the first reactor 11 using a column 12, a condenser 13, and the layer separator 14. Also, the lower discharge stream including the reaction product was supplied from the first reactor 11 into a second reactor 21 that was a reactor of a second reaction unit 20.

As in the operation flow in the first reaction unit 10, a continuous stirred tank reactor (CSTR) was operated through a second reaction unit 20, a third reaction unit 30, and a fourth reaction unit 40, and a lower discharge stream of a fourth reactor 41 that was a reactor of the last fourth reaction unit 40 was separated and refined to obtain dioctyl terephthalate.

In this case, a portion of the lower discharge stream including the alcohol was split from a layer separator in the third reactor 31 of the third reaction unit 30, and only a portion of the split stream was supplied into an upper portion of a third column 32 and passed through the third column. Thereafter, the portion of the split stream was refluxed into the third reactor 31, and a residual portion of the lower discharge stream of the layer separator, which was drawn off to the outside without being refluxed into the third reactor 31, was recycled as the feed stream of the first reactor 11.

Table 2 below lists the final conversion rate according to the draw-off ratio, which is a ratio of the flow rate of the lower discharge stream of the layer separator, which is drawn off to the outside without being refluxed into the third reactor 31, to the flow rate of the entire lower discharge stream including an alcohol from the layer separator of the third reactor 31, and a use amount of steam used during the entire process. In this case, the use amount of steam is represented by a relative amount with respect to a use amount (100.0%) of steam measured in Comparative Example 1 below.

Examples 3-1 to 3-4

A process of manufacturing dioctyl terephthalate (DOTP) was simulated using a commercially available process simulation program ASPEN PLUS (AspenTech) according to the process flow chart as shown in FIG. 7.

Specifically, a feed stream including terephthalic acid (TPA) and 2-ethylhexanol (2-EH) at a mole ratio of 1:2 to 4.5 was supplied into a first reactor 11 that was a reactor of a first reaction unit 10, and esterified in the presence of a catalyst to reflux all of a lower discharge stream including an alcohol from a layer separator 14 into the reactor 11 and remove water from an upper discharge stream vaporized in the first reactor 11 using a column 12, a condenser 13, and the layer separator 14. Also, the lower discharge stream including the reaction product was supplied from the first reactor 11 into a second reactor 21 that was a reactor of a second reaction unit 20.

As in the operation flow in the first reaction unit 10, a continuous stirred tank reactor (CSTR) was operated through a second reaction unit 20, a third reaction unit 30, and a fourth reaction unit 40, and a lower discharge stream of a fourth reactor 41 that was a reactor of the last fourth reaction unit 40 was separated and refined to obtain dioctyl terephthalate.

In this case, a portion of the lower discharge stream including the alcohol was split from a layer separator in the second reactor 21 of the second reaction unit 20, and only a portion of the split stream was supplied into an upper portion of a second column 22 and passed through the third column. Thereafter, the portion of the split stream was refluxed into the second reactor 21, and a residual portion of the lower discharge stream of the layer separator, which was drawn off to the outside without being refluxed into the second reactor 21, was recycled as the feed stream of the first reactor 11.

Table 3 below lists the final conversion rate according to the draw-off ratio, which is a ratio of the flow rate of the lower discharge stream of the layer separator, which is drawn off to the outside without being refluxed into the second reactor 21, to the flow rate of the entire lower discharge stream including an alcohol from the layer separator of the second reactor 21, and a use amount of steam used during the entire process. In this case, the use amount of steam is represented by a relative amount with respect to a use amount (100.0%) of steam measured in Comparative Example 1 below.

Examples 4-1 to 4-4

A process of manufacturing dioctyl terephthalate (DOTP) was simulated using a commercially available process simulation program ASPEN PLUS (AspenTech) according to the process flow chart as shown in FIG. 8.

Specifically, a feed stream including terephthalic acid (TPA) and 2-ethylhexanol (2-EH) at a mole ratio of 1:2 to 4.5 was supplied into a first reactor 11 that was a reactor of a first reaction unit 10, and esterified in the presence of a catalyst to reflux all of a lower discharge stream including an alcohol from a layer separator 14 into the reactor 11 and remove water from an upper discharge stream vaporized in the first reactor 11 using a column 12, a condenser 13, and the layer separator 14. Also, the lower discharge stream including the reaction product was supplied from the first reactor 11 into a second reactor 21 that was a reactor of a second reaction unit 20.

As in the operation flow in the first reaction unit 10, a continuous stirred tank reactor (CSTR) was operated through a second reaction unit 20, a third reaction unit 30, and a fourth reaction unit 40, and a lower discharge stream of a fourth reactor 41 that was a reactor of the last fourth reaction unit 40 was separated and refined to obtain dioctyl terephthalate.

In this case, a portion of the lower discharge stream including the alcohol was split from each of layer separators in each of the reactors, which span from the second reactor 21 of the second reaction unit 20 to the fourth reactor 41 of the fourth reaction unit 40, and only a portion of the split stream was supplied into an upper portion of each of columns and passed through the columns. Thereafter, the portion of the split stream was refluxed into the reactors, and a residual portion of the lower discharge stream of the layer separator, which was drawn off to the outside without being refluxed into the reactors, was recycled as the feed stream of the first reactor 11.

Table 4 below lists the final conversion rate according to the draw-off ratio, which is a ratio of the flow rate of the lower discharge stream of the layer separator, which is drawn off to the outside without being refluxed into each of the reactors, to the flow rate of the entire lower discharge stream including an alcohol from the layer separator of each of the reactors, and a use amount of steam used during the entire process. In this case, the use amount of steam is represented by a relative amount with respect to a use amount (100.0%) of steam measured in Comparative Example 1 below.

Comparative Example 1

A process of manufacturing dioctyl terephthalate (DOTP) was simulated using a commercially available process simulation program ASPEN PLUS (AspenTech) according to the process flow chart as shown in FIG. 9.

Specifically, a feed stream including terephthalic acid (TPA) and 2-ethylhexanol (2-EH) at a mole ratio of 1:2 to 4.5 was supplied into a first reactor 11 that was a reactor of a first reaction unit 10, and esterified in the presence of a catalyst to reflux all of a lower discharge stream including an alcohol from a layer separator 14 into the reactor 11 and remove water from an upper discharge stream vaporized in the first reactor 11 using a column 12, a condenser 13, and the layer separator 14. Also, the lower discharge stream including the reaction product was supplied from the first reactor 11 into a second reactor 21 that was a reactor of a second reaction unit 20.

As in the operation flow in the first reaction unit 10, a continuous stirred tank reactor (CSTR) was operated through a second reaction unit 20, a third reaction unit 30, and a fourth reaction unit 40, and a lower discharge stream of a fourth reactor 41 that was a reactor of the last fourth reaction unit 40 was separated and refined to obtain dioctyl terephthalate.

Table 4 below lists the final conversion rate, and a use amount of steam used during the entire process. In this case, the use amount of steam is represented by a relative amount with respect to the use amount (100.0%) of steam used in Examples.

TABLE 1

| | | Examples | | | |
|---|---|---|---|---|---|
| | | 1-1 | 1-2 | 1-3 | 1-4 |
| Fourth reactor | Conversion rate (%) | 97 | 96 | 96 | 96 |
| | Draw-off ratio (%) | 26 | 53 | 78 | 100 |
| Final conversion rate (%) | | 99 | 99 | 99 | 99 |
| Use amount of steam (%) | | 98 | 97 | 96 | 95 |

TABLE 2

| | | Examples | | | | | |
|---|---|---|---|---|---|---|---|
| | | 2-1 | 2-2 | 2-3 | 2-4 | 2-5 | 2-6 |
| Third reactor | Conversion rate (%) | 90 | 90 | 90 | 90 | 90 | 90 |
| | Draw-off ratio (%) | 24 | 46 | 68 | 78 | 88 | 99 |
| Final conversion rate (%) | | 99 | 99 | 99 | 99 | 98 | 98 |
| Use amount of steam (%) | | 98 | 96 | 94 | 93 | 92 | 92 |

TABLE 3

| | | Examples | | | |
|---|---|---|---|---|---|
| | | 3-1 | 3-2 | 3-3 | 3-4 |
| Second reactor | Conversion rate (%) | 81 | 80 | 80 | 80 |
| | Draw-off ratio (%) | 11 | 22 | 34 | 45 |
| Final conversion rate (%) | | 99 | 99 | 99 | 98 |
| Use amount of steam (%) | | 99 | 96 | 93 | 90 |

TABLE 4

| | | Comparative Example | Examples | | | |
|---|---|---|---|---|---|---|
| | | 1 | 4-1 | 4-2 | 4-3 | 4-4 |
| Second reactor | Conversion rate (%) | 81 | 81 | 81 | 80 | 80 |
| | Draw-off ratio (%) | 0 | 11 | 11 | 17 | 17 |
| Third reactor | Conversion rate (%) | 90 | 91 | 91 | 90 | 90 |
| | Draw-off ratio (%) | 0 | 10 | 20 | 21 | 21 |
| Fourth reactor | Conversion rate (%) | 97 | 97 | 96 | 96 | 96 |
| | Draw-off ratio (%) | 0 | 10 | 53 | 56 | 73 |
| Final conversion rate (%) | | 99 | 99 | 99 | 99 | 99 |
| Use amount of steam (%) | | 100 | 97 | 95 | 93 | 93 |

* Draw-off ratio: a ratio of a flow rate of a lower discharge stream of a layer separator, which is drawn off to the outside without being refluxed into each of reactors, to a flow rate of the entire lower discharge stream including an alcohol from a layer separator of each of the reactors Referring to Tables 1 to 4, it can be seen that the total use amount of energy used during the entire process was reduced because the entire lower discharge stream including the alcohol was refluxed from the layer separator of each of the first to fourth reactors into each of the reactors in the case of all of Examples, and the use amount of steam was reduced compared to 100.0% of the use amount of steam in the case of Comparative Example 1 in which the draw-off was not performed.

Specifically, referring to Examples 1-1 to 1-4 listed in Table 1 and Examples 2-1 to 2-4 listed in Table 2, it can be seen that there was no change in the final conversion rate even when the draw-off ratio increased because the conversion rate was already secured in the rear reactors (third to fourth reactors). That is, it can be seen that the final conversion rate of 99% was maintained even when the draw-off ratio reached 100% in the case of Examples 1-1 to 1-4, and the final conversion rate of 99% was maintained even when the draw-off ratio reached 78% in the case of Examples 2-1 to 2-4. Also, it can be seen that the use amount of steam was reduced up to 93% under the conditions at which the final conversion rate was maintained at 99%, compared to that of Comparative Example 1.

However, referring to Examples 2-5 and 2-6 listed in Table 2, even when the draw-off ratio was very high with 88% or more, the use amount of steam was reduced, and the final conversion rate was also reduced. Therefore, there were drawbacks such as reduced basic units of products and degraded product specifications.

Also, a case in which the draw-off was performed in the first reactor was not indicated in Tables. However, it was confirmed that, when the draw-off was performed in the first reactor, there was a poor effect of securing the reactivity because the excess ratio of the alcohol to the dicarboxylic acid in the reactor was maintained. Therefore, it was confirmed that the reactivity was able to be degraded due to the reduced excess ratio of the alcohol to the dicarboxylic acid in all of the reactors during the process, and thus there were problems regarding a decrease in the final conversion rate. In this case, the conversion rate in the first reactor was, for example, less than 50%, but the present invention is not limited thereto.

Meanwhile, referring to Examples 3-1 to 3-4 listed in Table 3, it can be seen that, when the draw-off was performed in the second reactor, the excess ratio of the alcohol in the subsequent reactors (third to fourth reactors) was changed, which had an influence on the final conversion rate. That is, it can be seen that, in the case of Examples 3-1 to 3-4, even when the draw-off ratio was 34%, the final conversion rate was maintained at 99%, and the final conversion rate was reduced to 98% even when the draw-off ratio was 45%. As a result, it can be seen that the use amount of steam was reduced up to 93% under the conditions at which the final conversion rate was maintained at 99%, compared to that of Comparative Example 1.

Also, referring to Table 4, it can be seen that, in the case of Examples 4-1 to 4-4 in which the draw-off was performed in all of the second to fourth reactors, the use amount of steam was also reduced up to 93% under the conditions at which the final conversion rate was maintained at 99%, compared to that of Comparative Example 1.

Therefore, it was confirmed according to the present invention that the total use amount of energy during the process was reduced, compared to that of Comparative Example 1 in which the draw-off was not performed, by supplying the upper discharge stream of at least one reactor of the second to $n^{th}$ reactors into each of the layer separators, splitting a portion of the lower discharge stream including the alcohol from each of the layer separators to reflux a portion of the lower discharge stream, and drawing off a residual portion of the lower discharge stream, wherein the draw-off ratio was adjusted according to the reaction conditions such as the temperature and pressure of the reactors, and the retention time of the reactants, and the like.

The invention claimed is:

1. A method of manufacturing a diester-based compound, which is performed using a continuous process comprising a reaction part in which a total of n reaction units spanning from a first reaction unit to an $n^{th}$ reaction unit are connected in series, wherein each of the reaction units comprises a reactor, a column, and a layer separator, and the method comprises:

step s10: supplying a feed stream comprising a dicarboxylic acid and an alcohol into a first reactor of the first reaction unit, esterifying the feed stream to prepare a reaction product, and supplying a lower discharge stream of the first reactor comprising the reaction product into a second reactor of a second reaction unit;

step s20: supplying an upper discharge stream of the first reactor into the column of the first reactor to reflux in the column, and an upper discharge stream of the column is supplied to the layer separator of the first reaction unit, and a lower discharge stream comprising an alcohol from the layer separator is supplied into the first reactor through the column of the first reactor; and step s30: supplying an upper discharge stream of the second to the $n^{th}$ reactors into each of the columns of the second to $n^{th}$ reactors to reflux in the column, supplying an upper discharge streams of each the columns of the second to $n^{th}$ reactors to each of layer separators of the second to the $n^{th}$ reactors, splitting a portion of the lower discharge stream comprising the alcohol from each of the layer separators, and feeding back only a portion of the split stream into each of the second to the $n^{th}$ reactors through the column of each of the second to the $n^{th}$ reactors, wherein in the step s30, a draw-off ratio calculated below is controlled based on temperature and pressure and/or retention time of the dicarboxylic acid and the alcohol of each of the first to the $n^{th}$ reactors:

the draw-off ratio=

(a ratio of a flow rate of the lower discharge stream of the layer separator, which is drawn off without being feeding back into the reactor)/

(a flow rate of an entire amount of the lower discharge stream).

2. The method of claim 1, wherein the at least one reactor is a reactor in which a conversion rate reaches 50 to 99% among the second reactor to the nth reactor.

3. The method of claim 1, wherein, in the step s30, an upper discharge stream comprising an alcohol and water is supplied from each of the first to the $n^{th}$ reactors into the column of each of the first to the $n^{th}$ reactors to perform a gas/liquid separation, a gas phase is condensed as the upper discharge stream and supplied into the layer separators of the first to the $n^{th}$ reactors, and only a portion of the split stream obtained from the layer separators is supplied as a lower discharge stream into each of the second to the $n^{th}$ reactors through the column of the second to $n^{th}$ reactors.

4. The method of claim 1, wherein the upper discharge stream comprising an alcohol and water is supplied from the first to n−1 st reactors into the column of the first to n−1st reactors to perform a gas/liquid separation, the gas phase is condensed as the upper discharge stream and supplied into the layer separators of the first to n−1st reactors, and the liquid phase is supplied as the lower discharge stream into each of the first to n−1st reactors through the column of the first to n−1st reactors, and only a portion of the split stream obtained by splitting the lower discharge stream comprising the alcohol from each of the layer separator is supplied into each of the first to n−1st reactors through the column of the first to n−1st reactors.

5. The method of claim 3, wherein a water layer and an alcohol layer are separated in the layer separators, and only a portion of the split stream obtained by splitting the lower discharge stream comprising the alcohol from each of the layer separators is supplied into an upper portion of the column to pass through the column, and then refluxed into each of the reactors.

6. The method of claim 1, wherein a mole ratio of the dicarboxylic acid and the alcohol in the feed stream is in a range of 1:2 to 1:10.

7. The method of claim 1, wherein, in the step s30, a portion of the lower discharge stream comprising an alcohol is split from each of the layer separators and only a portion of the split stream is refluxed into each of reactors, and the residual stream of the lower discharge stream in each of the layer separators is recycled as the feed stream.

8. The method of claim 1, wherein n is in a range of 2 to 8.

9. The method of claim 1, wherein the dicarboxylic acid comprises terephthalic acid, and the alcohol comprises 2-ethylhexanol.

10. The method of claim 4, wherein a water layer and an alcohol layer are separated in the layer separators, and only a portion of the split stream obtained by splitting the lower discharge stream comprising the alcohol from each of the layer separators is supplied into an upper portion of the column to pass through the column, and then refluxed into each of the reactors.

11. The method of claim 1, wherein the draw-off ratio is in a range from 24% to 99%.

12. The method of claim 1, wherein the draw-off ratio is in a range from 11% to 45%.

13. The method of claim 1, wherein the draw-off ratio is in a range from 11% to 17%.

* * * * *